(12) United States Patent
Madere

(10) Patent No.: US 11,918,499 B1
(45) Date of Patent: Mar. 5, 2024

(54) ANTI-TREMOR ORTHOTIC SYSTEM

(71) Applicant: Krista Madere, Gonzales, LA (US)

(72) Inventor: Krista Madere, Gonzales, LA (US)

(*) Notice: Subject to any disclaimer, the term of this patent is extended or adjusted under 35 U.S.C. 154(b) by 643 days.

(21) Appl. No.: 15/041,073

(22) Filed: Feb. 11, 2016

Related U.S. Application Data

(60) Provisional application No. 62/176,251, filed on Feb. 12, 2015.

(51) Int. Cl.
*A61F 5/01* (2006.01)
*A61H 99/00* (2006.01)

(52) U.S. Cl.
CPC ............ *A61F 5/0118* (2013.01); *A61H 99/00* (2013.01); *A61H 2201/0165* (2013.01)

(58) Field of Classification Search
CPC .... A61F 5/0118; A61F 5/0104; A61F 5/0102; A61F 5/01; A61F 5/058; A61F 5/05841; A61F 5/05858; A61F 5/05866; A61F 5/30; A61F 5/32; A61F 5/34; A61F 13/00; A61F 13/00004; A61F 13/00021; A61F 2013/0028; A61F 5/04; A61F 13/04; A61F 13/041; A61F 5/013; A61B 34/75; A61B 5/1101; A61H 2205/06; A41D 13/088; A41D 13/084; A41D 13/082; A41D 13/081; A41D 13/08; A41D 13/05; A63B 21/06; A63B 21/065; A63B 21/4001; A63B 21/4017; A63B 21/4019; A63B 21/4021; A63B 23/16
See application file for complete search history.

(56) References Cited

U.S. PATENT DOCUMENTS

| | | | | |
|---|---|---|---|---|
| 19,814 | A * | 3/1858 | Monestier | |
| 4,109,908 | A * | 8/1978 | Pugh | A63B 21/065 482/105 |
| 4,247,097 | A * | 1/1981 | Schwartz | A63B 21/065 2/158 |
| 4,911,433 | A * | 3/1990 | Walker | A63B 21/065 2/161.1 |
| 5,003,637 | A * | 4/1991 | Lonon | A41D 19/0024 2/160 |
| 5,184,815 | A * | 2/1993 | Maddox | A63B 69/0002 2/161.1 |
| 6,035,443 | A * | 3/2000 | Green | A63B 71/146 2/161.2 |
| 6,553,574 | B1 * | 4/2003 | Hall, Jr. | A63B 21/065 2/160 |
| 6,990,689 | B1 * | 1/2006 | Thellmann | A63B 21/065 2/161.1 |
| 7,081,102 | B1 * | 7/2006 | Koetter | A61F 5/013 128/878 |
| 2003/0078530 | A1 * | 4/2003 | Wolfe | A61F 5/0118 602/21 |

(Continued)

OTHER PUBLICATIONS

Dictionary.com, "digit," https://www.dictionary.com/browse/digit.*

*Primary Examiner* — Victoria Hicks Fisher
(74) *Attorney, Agent, or Firm* — Andrew Vicknair

(57) ABSTRACT

An anti-tremor orthotic system is disclosed for reducing tremors in individuals with various medical conditions. A user can utilize the present invention as a means to reduce tremors without having to reduce or restrict daily activities or the functional range of motion of their arms and hands when in use.

2 Claims, 12 Drawing Sheets

(56) References Cited

U.S. PATENT DOCUMENTS

2007/0100266 A1* 5/2007 Hargrave ................ A61F 5/012
            602/21
2014/0343469 A1* 11/2014 Bush ..................... A61F 13/043
            602/1

* cited by examiner

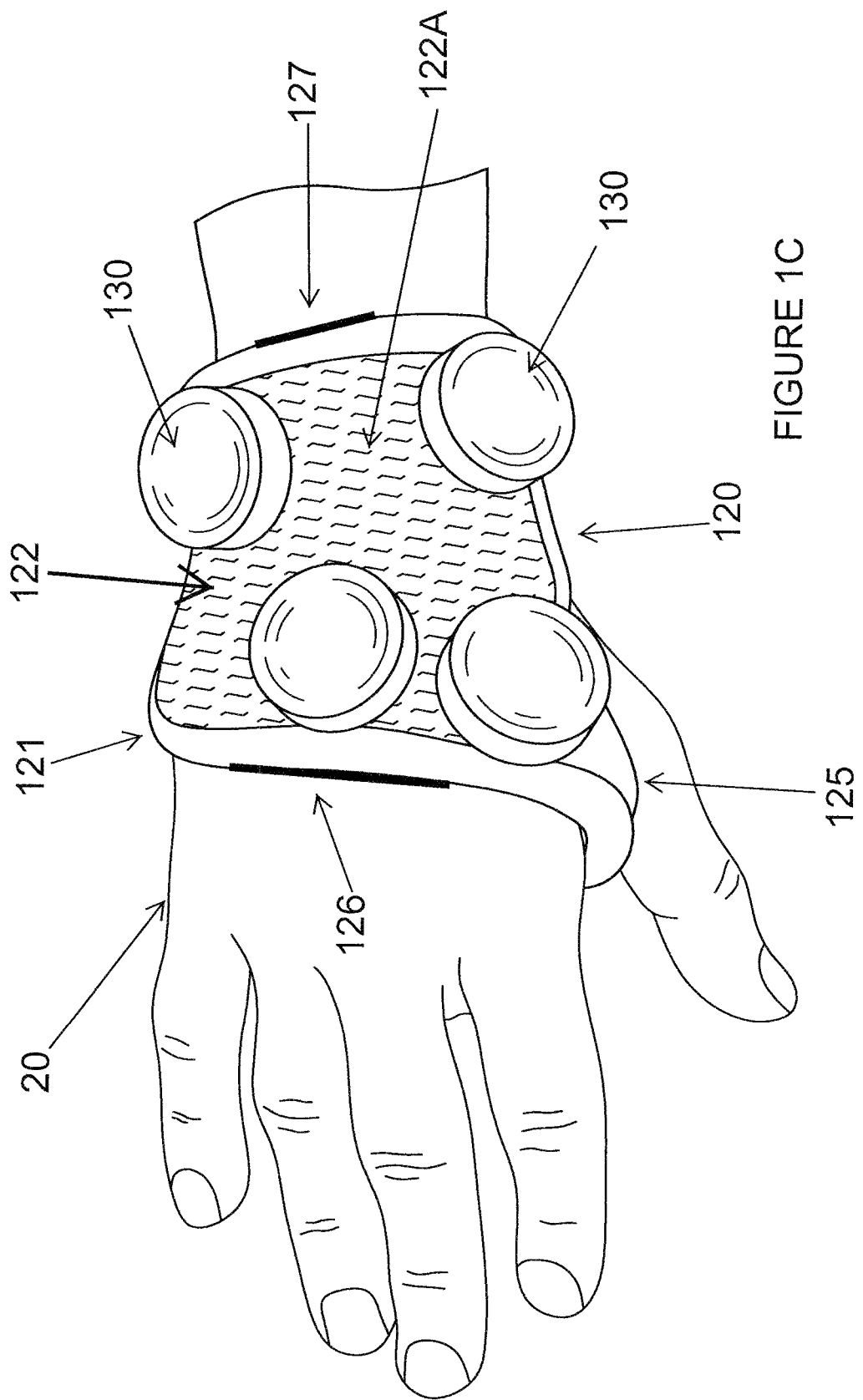

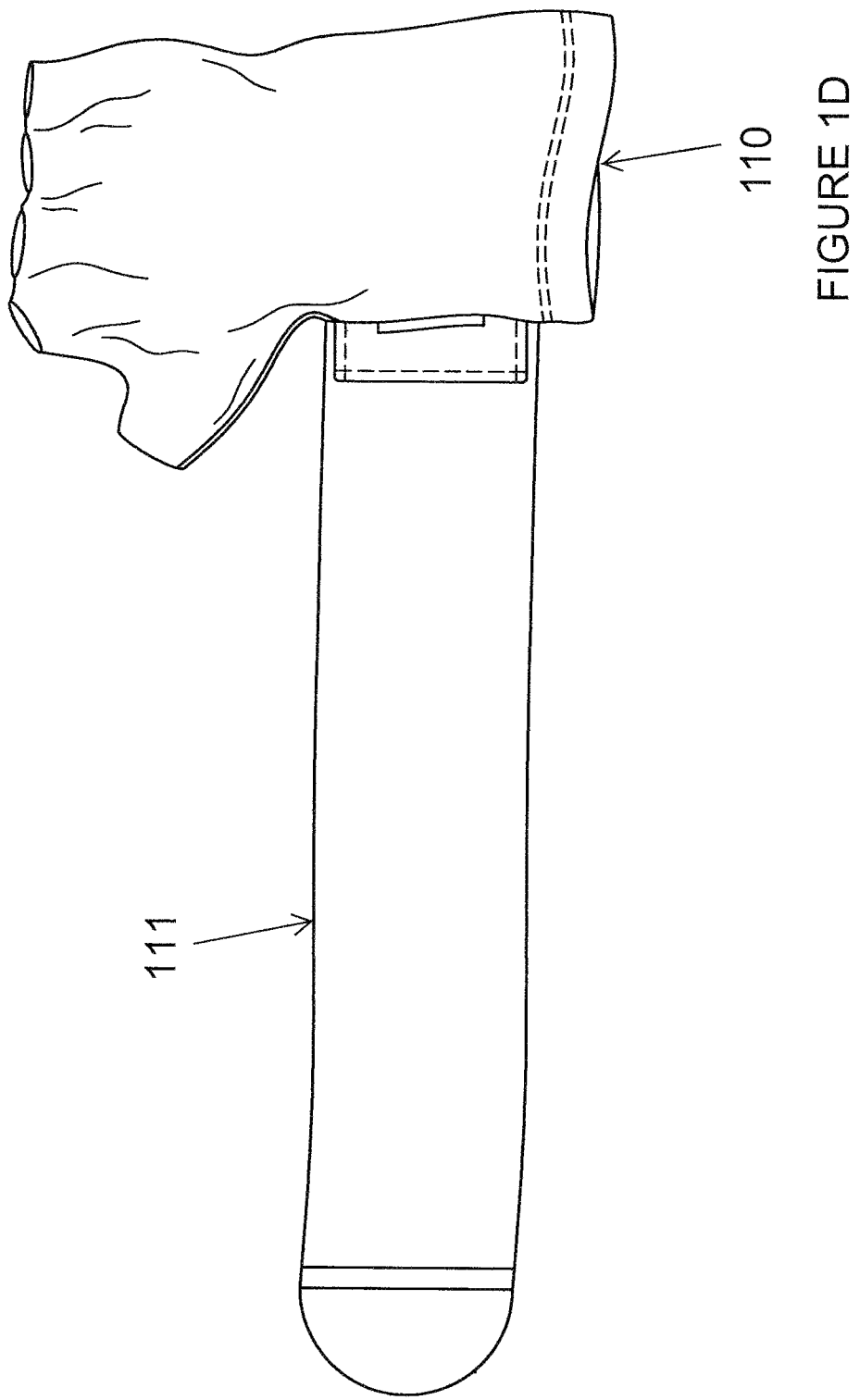

ANTI-TREMOR ORTHOTIC SYSTEM

CROSS REFERENCE TO RELATED APPLICATION

This application claims the benefit of U.S. provisional application Ser. No. 62/176,251 filed on Feb. 12, 2015.

TECHNICAL FIELD OF INVENTION

The present invention relates, in general to a device utilized to assist in preventing and/or reducing tremors in individuals experiencing tremors of the hands and lower arms.

BACKGROUND OF INVENTION

Everyday life often entails the use of one's hands numerous times over the course of an ordinary day. While the use of one's hands is an easy task for a majority of individuals, numerous individuals struggle with the daily life and the required use of their hands due to various tremor disorders and conditions. Currently, numerous individuals experience tremors on a daily basis due to various medical conditions including, but not limited to, mild to severe hand tremors, Parkinson's disease, Essential Tremor, dystonic tremor, resting tremor, action tremor, cerebellar tremors, various psychological disorders, and tremors associated with medication side effects. In the United States, 7 million people have been diagnosed with Essential Tremor while at least 4 million are undergoing treatment. Due to these tremors, individuals are limited in their activities, often need assistance of some kind, and are also embarrassed when attempting to perform certain tasks due to the tremors.

Individuals experiencing such tremors often experience difficulty eating, driving, typing, writing, brushing teeth, holding objects, and are sometimes unable to perform certain tasks depending upon the severity of the tremors. Some individuals suffering from tremors can be treated with medication and/or surgery; however, not every individual experiencing tremors can experience relief through medication or surgery. And while some devices exist to help those individuals with the tremors, the devices are activity specific. For instance, weighted pens for assistance with writing and specialized eating utensils have been developed to cancel and/or reduce the effects of tremors to assist tremor patients with writing and eating. However, such devices are limited to aiding tremor patients with specific tasks, such as writing and eating, but they do not assist tremor patients with performing other activities, such as driving, holding a TV remote control, using a touch screen computer device, typing, brushing teeth, sewing, threading needles, crocheting, needle point, using scissors, and other activities.

While some relief is available for individuals experiencing or suffering with tremors, there is no single device to address the tremors and aid said individuals in any activity that they choose. Accordingly, a need exists in the art for a system and method that can control or lessen tremors that can be used by tremor patients to assist the patient with performing any activity.

BRIEF SUMMARY OF THE INVENTION

The present invention is an anti-tremor orthotic system and method for reducing tremors that will assist in reducing tremors in patients experiencing tremors so that said individuals may perform tasks with less difficulty. In one embodiment, the anti-tremor orthotic system may include a rigid or prefabricated custom hand base, a plurality of weights securely fastened to the base, and a covering member that covers the weights and a portion of the base member or the entire base member. In this embodiment, the weights and cover components are arranged to reduce the tremors so that the user will have less difficulty performing certain activities, such as eating, typing, writing, brushing teeth, sewing, threading a needle, crocheting, using tools, and the like. In another embodiment, the present invention may also include the addition of one or more rigid support members positioned across or near the wrist to further stabilize and reduce the tremors.

In another embodiment of the present invention, the anti-tremor orthotic system may include a rigid custom or prefabricated forearm base, a plurality of weights securely fastened to the forearm base, and a covering member to cover the forearm base and weights. The present invention may also include a cover that is configured to cover the forearm and/or the elbow to further assist in reducing tremors.

In another embodiment of the present invention, the anti-tremor system may include a rigid custom or prefabricated hand base with weights, a rigid custom or prefabricated forearm base with weights, an optional rigid wrist support, and one compression member for fastening all components to a patient's hand and forearm area and for securely fastening any weights. The single compression member is advantageous as it can secure all components to a user's hand/arm and may also act to cover the various components attached to a user. This embodiment will reduce the user's tremors such that a user will experience less difficulty in carrying out everyday activities, including, but not limited to eating, driving, writing and typing.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIG. 1C is another illustration of a portion of the present invention illustrated in of FIG. 1 located on a user's hand;

FIG. 1D is an illustration of a portion of the present invention;

DETAILED DESCRIPTION OF THE INVENTION

Referring now in more detail to the drawings, the present invention will now be described in more detail.

Figure 1:
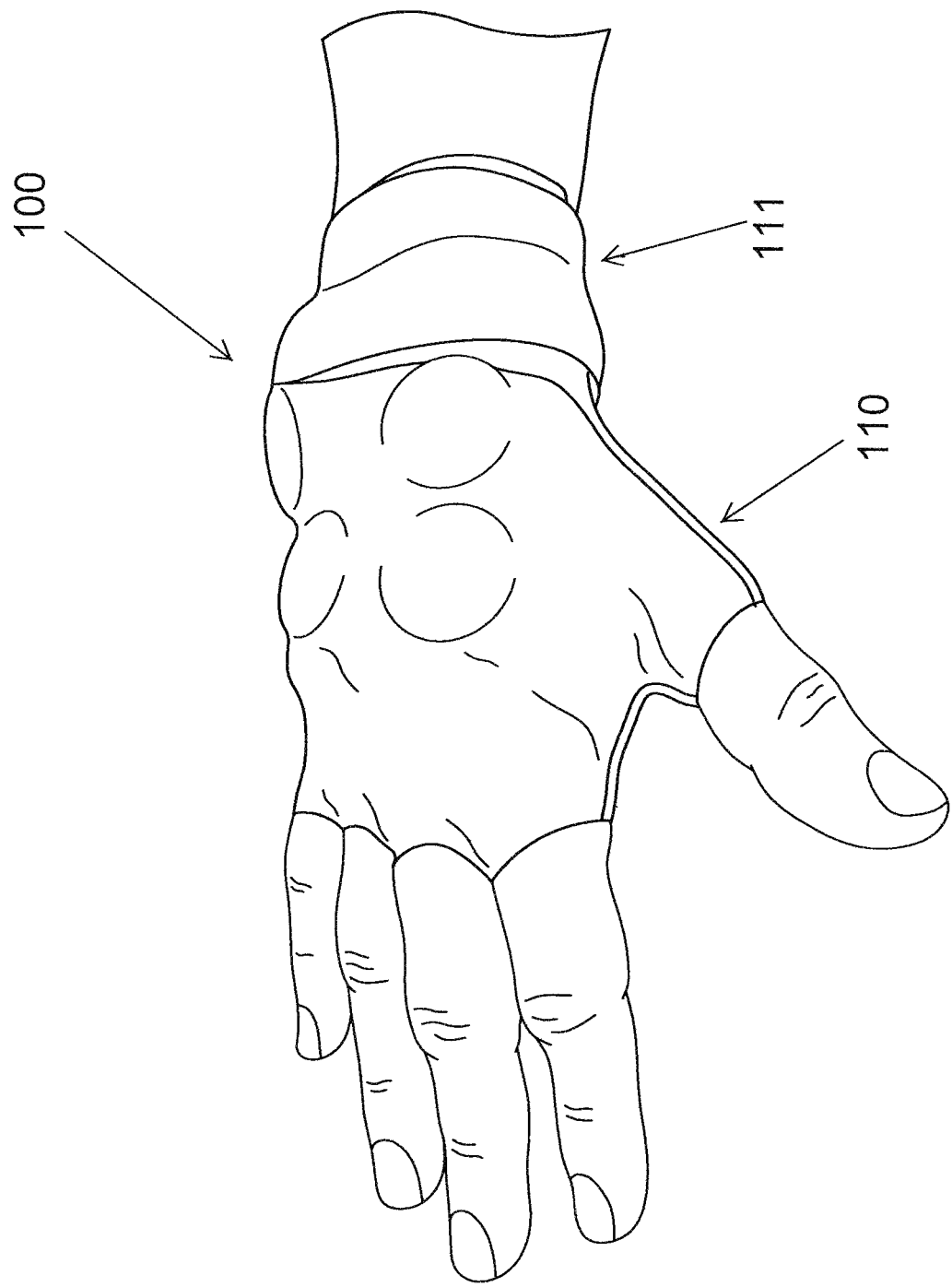
FIG. 1 is an illustration of one embodiment of the present invention.
Figure 1A:
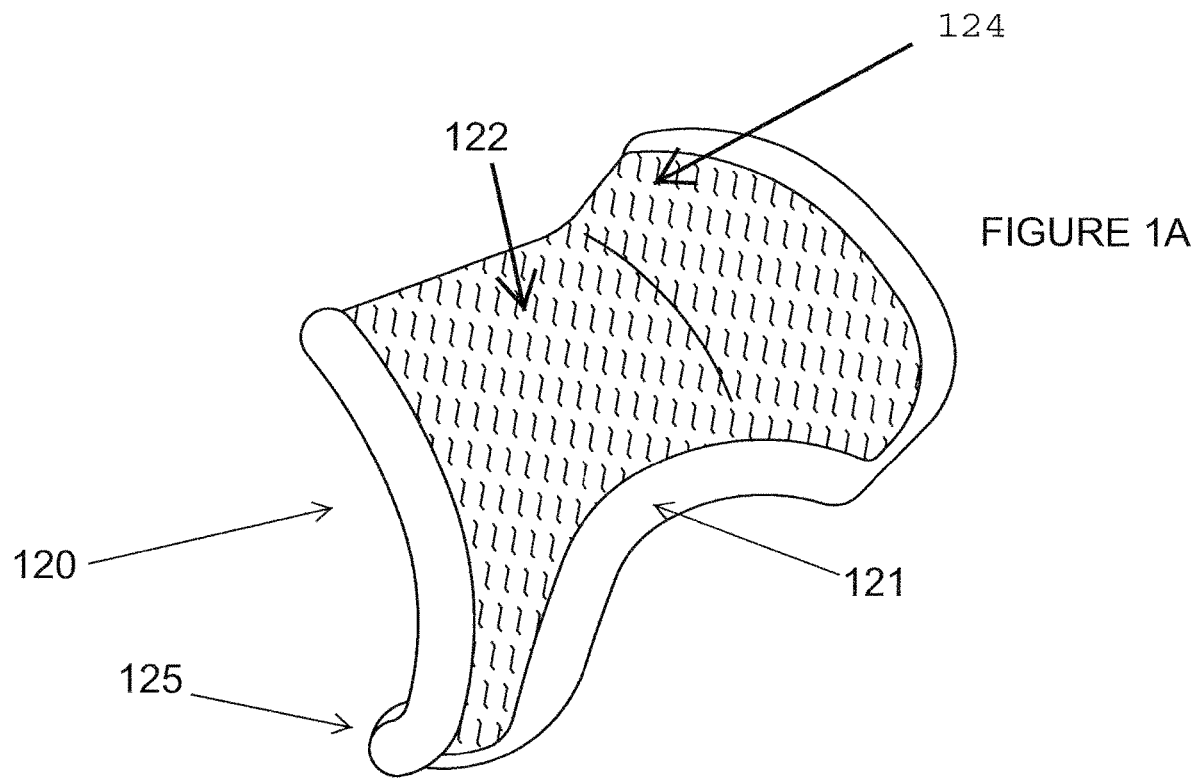
FIG. 1A is an illustration of a portion of the present invention illustrated in FIG. 1.
Figure 1B:
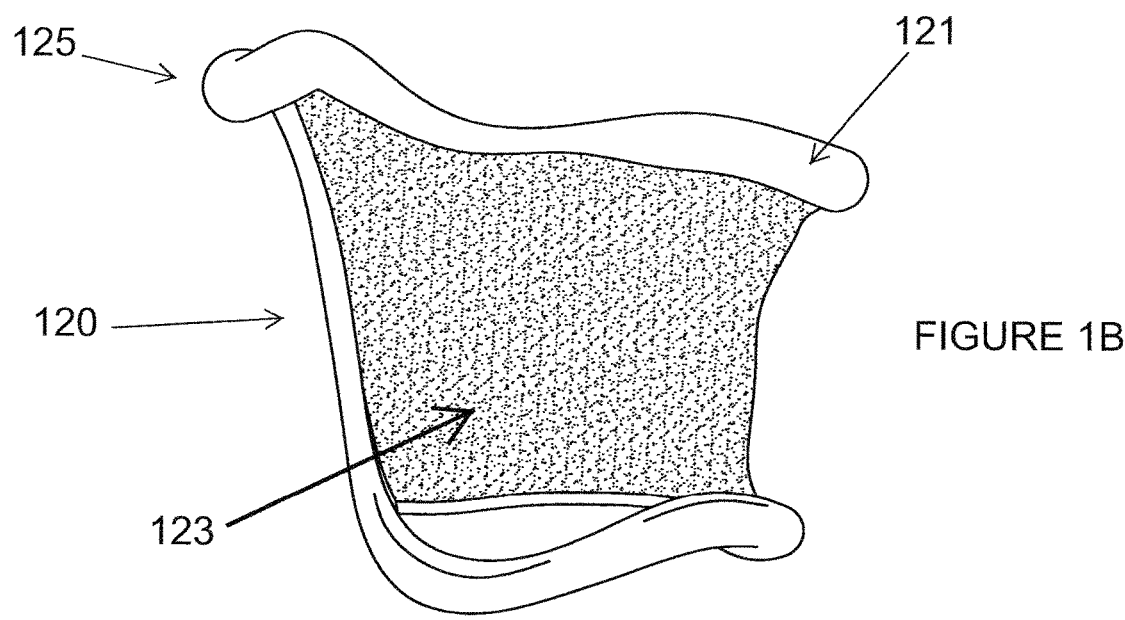
FIG. 1B is another illustration of a portion of the embodiment illustrated in of FIG. 1.

FIG. 1 illustrates a view of one embodiment of the present invention. The anti-tremor orthotic system 100 in FIG. 1 is illustrated with a cover member 110 positioned over various components that are illustrated in FIGS. 1A-1C. In a preferred embodiment, the various components of orthotic system 100 work together to reduce flexion/extension tremors of a user's wrist and digits. FIG. 1A illustrates an overhead view of a dorsal base member 120, FIG. 1B illustrates an underside view of dorsal base member 120, and FIG. 1C illustrates another overhead view of dorsal base member 120 positioned on a user with weighted members 130 connected to base member 120. As illustrated in FIGS. 1A-1C, the anti-tremor orthotic system 100 is preferably configured with a base member 120. In one embodiment, base member 120 is configured with a volar expansion member 125 as illustrated in FIGS. 1A-1C. Expansion member 125 follows the anterior curvature of the hand and fits between an individual's thumb and index finger into the web space or purlicue between the thumb and index finger. By spanning into this web space, expansion member 125 helps to prevent migration or rotation of base member 120 and also helps to provide a good fit for base member 120 of anti-tremor orthotic system 100. As illustrated in FIG. 1, the anti-tremor orthotic system 100 is configured so that it does not cover a user's fingers.

In one embodiment of the present invention, base member 120 is configured with at least one flared out area 124 as shown in FIG. 1A. Flared out area 124 is a section of base member 120 that projects posteriorly to account for the ulnar styloid bone so that base member 120 will not constantly rub against the ulnar styloid bone. Flared out area 124 will reduce pressure on the ulnar styloid bone when a user moves his/her wrist and will allow a user's ulnar styloid bone to clear base member 120 without causing irritation, causing pain, or causing skin tearing at the ulnar styloid process. In alternative embodiments, base member 120 may be configured to account for any bony landmarks to cut-down and reduce any irritation that could exist from base member 120 constantly rubbing against a user's bones.

Base member 120 is configured to fit over a portion of an individual's hand/wrist area on the dorsum or back side of an individual's hand. Base member 120 has a distal edge 126 located near a user's phalanges or fingers and a proximal edge 127 located near a user's wrist. In one embodiment, the present invention is also configured so that base member 120 is sized so that the carpometacarpal joints (CMC), the thumb metacarpophalangeal (MP) joint, and the thumb interphalangeal (IP) joint are free and not hindered by base member 120. In another embodiment, the present invention may be configured so that base member 120 covers or crosses the carpometacarpal joints (CMC), the thumb metacarpophalangeal (MP) joint, and/or the thumb interphalangeal (IP) joint. Thus, in such an embodiment, base member 120 would further reduce flexion/extension tremors and would minimally limit range of motion towards extension, but still allow a user to experience full functional range of motion for grasp and prehension.

Base member 120 is also configured such that it is made of some type of rigid material, such as thermoplastic, to provide some counterforce or resistance to abnormal movements of the hand. Base member 120 is also specially sized so that when in use, distal edge 126 of base member 120 sits near the metacarpophalangeal (MCP) joints in a user's hand. This configuration and placement of base member 120 in combination with weighted members 130 allows the location and placement of weighted members 130 to constantly assist in reducing tremors by producing a counterforce and sensory inhibition and creating a fulcrum and an inhibition of the superficial extensor tendons on the back of the user's hand to reduce a user's tremors.

In one embodiment of the present invention, as illustrated in FIGS. 1A—1C, base member 120 may also include a cushioning area 121 that surrounds the outer boundaries or edges of base member 120 to provide comfort to its user. Cushioning area 121 may be an area of base member 120 that includes foam or some other soft material to provide a soft or cushioning feeling to a user for the purpose of providing comfort to a user. In one embodiment, cushioning area 121 may be configured with a thickness and height to provide space between base member and a user's skin to allow for air flow between base member 120 and user's skin to assist in reducing the amount of perspiration to increase a user's comfort level.

As illustrated in FIG. 1A, base member 120 is also configured with a landing area 122 located on the outer side of base member 120. Landing area 122 provides an area for the placement of weighted members 130 as illustrated in FIG. 1C. In one embodiment of the present invention, base member 120 is configured so that landing area 122 is covered with some type of fastening material that is attached to the back side of base member 120 and is suitable for receiving and holding various types of weighted members 130 as illustrated in FIG. 1C.

FIG. 1B illustrates an underside view of base member 120. The underside of base member 120 includes an underside cushioning area 123. Underside cushioning area 123 is an area of base member 120 that will likely come into contact with the skin of the opisthenar, dorsum, or back portion of a user's hand when in use. In one embodiment, cushioning area 123 is configured so that it includes foam or some other soft material to provide a soft or cushioning surface so that when base member 120 is in use, a user will feel the softness of cushioning area 123. While foam may be used to provide comfort to a user at cushioning area 123, the present invention is not limited to foam, such as closed cell foam, as any number of soft materials may be used to provide cushioning, such as cotton, gel packs, felt, bubble materials, and the like.

FIG. 1C illustrates another overhead shot of base member 120 positioned on the opisthenar, dorsum, or back portion of a user's hand 20 with weighted members 130 connected to landing area 122 of base member 120. Weighted members 130 may be configured in any number of different shapes and sizes. Weighted members 130 in conjunction with base member 120 work together to provide at least a counterforce to movement and a sensory inhibition to the superficial extensor tendons and/or pollicus abductor tendons and/or intrinsic hand muscles on the back of the hands and may provide some minimal inhibition to movement to the joints.

Arrangement and placement of weighted members 130 to base member 120 is beneficial to users in that such arrangement assists in reducing a user's tremors and provides various therapeutic benefits resulting from use of anti-tremor orthotic system 100. Use of anti-tremor orthotic system 100 will improve and increase a user's strength and increase a user's muscle mass from resistance created by the various components of anti-tremor orthotic system 100. The increase in muscle mass from use of anti-tremor orthotic system 100 will further assist in decreasing a user's tremors.

In one embodiment of the present invention, as illustrated in FIG. 1C, weighted members 130 are cylindrical disks made of some type of non-toxic materials, such as aluminum or stainless steel, that are configured in 2 ounce increments for ease of placement and removal. However, the present invention is not limited to this configuration as weighted members 130 may be configured in any other configurations and may be made of plastic or any other materials and may be configured in any number of different shapes and any number of weight increments.

In one embodiment, landing area 122 may be configured with any number of different fastening materials to create a connection membrane for securing items such as weighted members 130 and allowing weighted members 130 to be easily moved, removed, replaced, or additional weighted members 130 added with little to no difficulty. In one embodiment of the present invention, landing area 122 may be configured with a fastening material such as hook and loop fasteners illustrated as 122A in FIG. 1C whereby one component of the hook and loop fasteners, such as the hooks, is attached to landing area 122 and the second component of the hook and loop fastener, such as the loops, is attached to weighted members 130 so that weighted members 130 may be securely connected to landing area 122 of base member 120. The weighted member 130 is positioned directly on the landing area 122 of the outer side of base member 120. In alternative embodiments, landing area 122 may be configured so that the surface of landing area 122 is magnetic and weighted members 130 are also magnetic so that weighted members 130 may be magnets which would allow a user to easily remove and add additional magnets in a quick and easy manner to accommodate a user's needs to add or remove weighted members 130 as needed.

In one embodiment, the present invention is configured so that weighted members 130 may be easily removed or moved to different locations on landing area 122 of base member 120. The ability to easily remove weighted members 130 on base member 120 allows users to utilize proper size weighted members based on a "less is more" selection. For instance, if the present invention is configured with too many weighted members 130, a user could experience fatigue which could worsen the tremor. Thus, the present invention allows a user to easily remove weighted members 130 to achieve optimal results.

In addition, weighted members 130 may be easily removed and replaced with different size weighted members 130 (heavier or lighter). Different size weighted members 130 may be used to replace or add to any existing weighted members 130 to assist with the effectiveness of reducing tremors based on various factors that may affect the severity of a user's tremors. For instance, a user's tremors may increase or decrease based on the amount of sleep or lack thereof, level of stress, medication treatment, and the like. And depending upon the severity of tremors that a user is experiencing, the present invention enables a user to easily select different size weighted members 130 and arrange weighted members 130 in a configuration that provides a "just right" amount of weight to effectively target and reduce the user's tremors.

In a preferred embodiment, weighted members 130 are arranged on base member 120 near the muscle groups and/or near extrinsic tendons that are contracting excessively and/or involuntarily. As illustrated in FIG. 1C, weighted members can be moved about landing area 122 of base member 120 so that user may obtain optimal performance and increased tremor reduction by arranging weighted members 130 near the targeted muscle groups and/or tendons that experience excessive contracting.

In alternative embodiments of the present invention, base member 120 may be configured with a series of slots or grooves in landing area 122 that may run horizontal or vertical. These slots or grooves would provide a location for weights 130 to be mounted to base member 120. In such an embodiment, weights 130 would preferably be configured with a tongue or extension member that extends out from weighted member 130 and is sized to fit in the slots or grooves in landing area 122. In another embodiment, the present invention may be configured so that weighted members 130 and base member 120 connect to one another utilizing a tongue-in-groove configuration. The use of such connection mechanisms allows weighted members 130 to be easily removed from base member 120 and enables the weighted members 130 to be reconfigured and moved from one location to another as needed by a user to control and reduce the tremors experienced by the user. In other embodiments, the present invention may be configured so that base member 120 has a series of female holes or openings configured to receive some type of male component that is attached to weighted members 130 so that a user may simply "plug" weighted members 130 into any of a series of female holes or openings or connector parts located on base member 120. The above referenced connection mechanisms are merely examples and are not limitations upon the present invention as any number of connection mechanisms or systems may be used to connect weighted members 130 to base member 120.

FIG. 1D illustrates cover member 110 of anti-tremor orthotic system 100. As illustrated, cover member 110 is preferably in the shape of a glove that is configured to slide over the hand and fingers and fit over and cover base member 120 and weighted member(s) 130. While cover member 110 is illustrated in FIG. 1D as fingerless and not extending over and covering a user's fingers, the present invention is not limited to this configuration. In alternative embodiments, cover member 110 may be full-fingered to completely cover a user's fingers and may also include various traction members or grip assist members that may be mounted on the finger-tip portions of such a cover member 110 to provide grip assistance to users. Cover member 110 also assists in holding base member 120 and weighted members 130 in the various strategic locations needed to reduce tremors in patients, such as holding base member 120 and weighted members 130 at the dorsal aspect of the hand near the metacarpophalangeal (MCP) joints. In such a configuration, cover member 110 protects anti-tremor orthotic system 100 and enables a user or patient utilizing anti-tremor orthotic system 100 to have an unrestricted or minimally restricted range of motion. A user is thus able to partake in all daily activities and any number of hobbies without having to worry about any functional limitations in range of motion. Cover member 110 is also configured so that it holds weighted members 130 in place so that anti-tremor orthotic system 100 can continue to provide an inhibition and counterforce to the superficial extensor and abductor tendons. Such an embodiment of anti-tremor orthotic system 100 functions to control tremors while at the same time allowing users/patients to enjoy their daily lives.

As illustrated in FIGS. 1 and 1D, cover member 110 may also be configured with strap 111. Strap 111 provides an additional level of support for securing cover member 110 to a user's hand and supporting the wrist unrestricted. In one embodiment, strap 111 may be an elastic strap that is part of cover member 110 and when in use, strap 111 wraps around a user's wrist and is secured to cover member 110 or other portions of strap 111 with hook and loop fasteners (Velcro) or some other fastening means. Cover member 110 is preferably comprised of some type of nylon, neoprene, and/or spandex material so that cover member 110 will provide some level of compression and fit snuggly around a user's wrist, but will not be overly tight or discomforting to a user. However, the present invention is not limited to this configuration as in other embodiments, cover member 110 may be made of different types of materials, such as cloth, wool, leather, rubber, latex along with some additional components to assist in holding cover member 110 securely over base member 120 and weighted members 130. In one embodiment, base member 120 is comprised of some form of thermoplastic. However, the present invention is not limited by this preferred material as base member 120 may be made of any number of various materials, such as metal, plastic, Teflon, chrome, stainless steel, aluminum, any combination thereof, and the like.

The components of anti-tremor orthotic system 100 illustrated in FIGS. 1 and 1A-1D operate to reduce tremors in users. As illustrated in FIGS. 1 and 1A-1D, the combination and arrangement of these various components of anti-tremor orthotic system 100 (weighted members 130, base member 120, and cover member 110) work together to produce a sensory inhibition and create a fulcrum and a counterforce to the superficial extensor and abductor tendons on the back of the user's hand to reduce a user's tremors. The specific configuration and arrangement of the components of the present invention may be specifically altered for each specific user to achieve such inhibition and fulcrum.

Figure 2A:
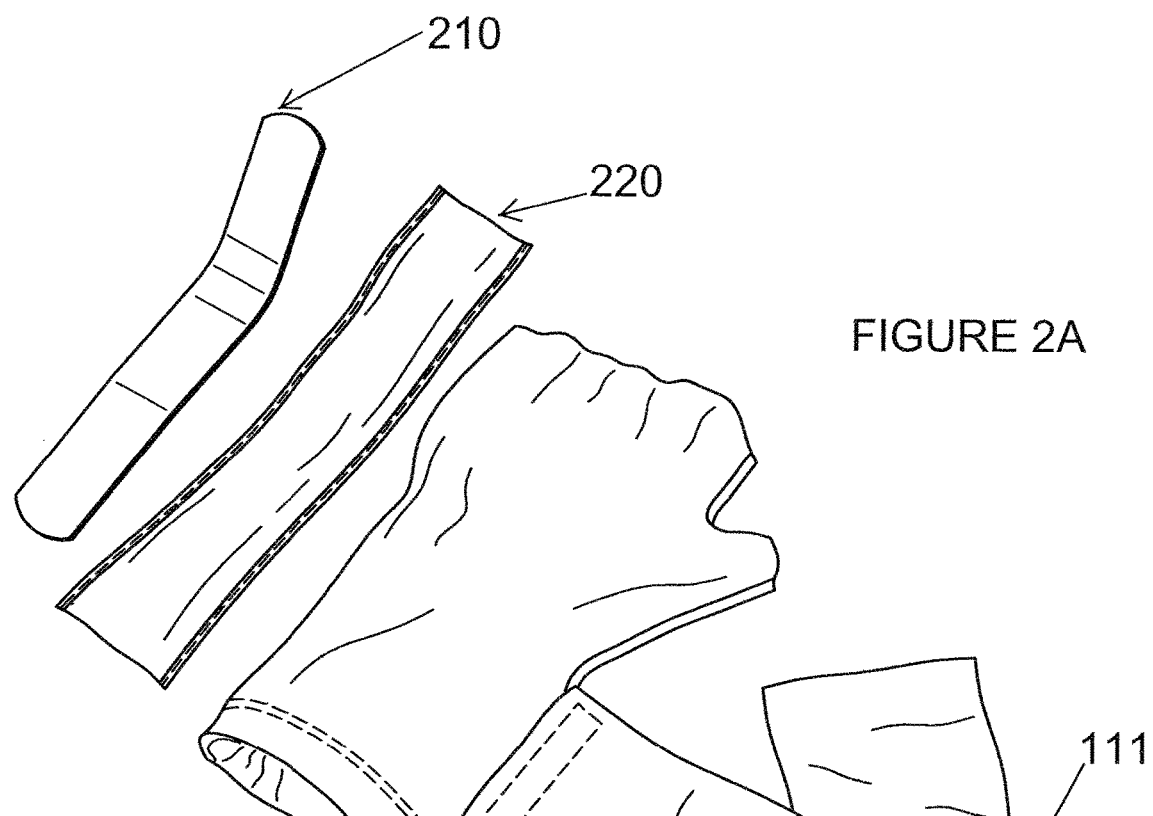
FIG. 2A is an illustration of a portion of an alternative embodiment of the present invention.
Figure 2B:
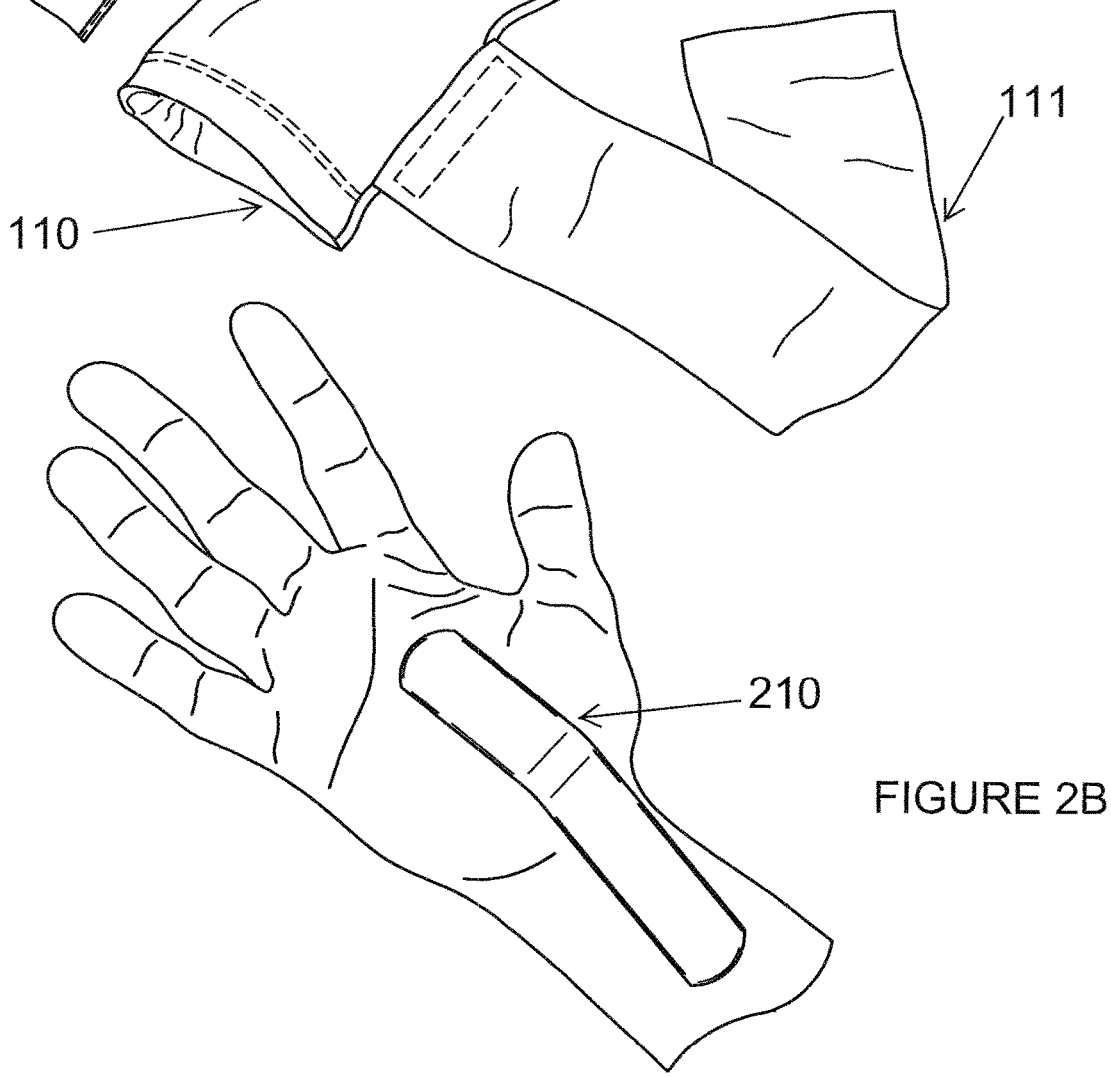
FIG. 2B is an illustration of a component of the alternative embodiment of FIG. 2A.

FIG. 2A illustrates an embodiment of the present invention configured with a rigid wrist support 210. Rigid wrist support 210 is configured to contour with and fit the natural shape of the wrist to the palm of the hand as illustrated in FIG. 2B. FIG. 2B is an illustration of rigid wrist support 210 aligned with the transition from a user's forearm to the wrist to the palm of the hand. In one embodiment, the present invention is configured with a pocket member 220 for holding rigid wrist support 210. Pocket member 220 is preferably attached to the inside of cover member 110. With pocket member 220 attached to the inside of cover member 110, wrist support 210 will remain in place for a user and help provide additional support for a user needed to assist in reducing tremors. Rigid wrist support 210 also acts to immobilize and support a user's wrist when it is installed in anti-tremor orthotic system 100. In one embodiment, rigid wrist support 210 is made of some type of metal, such as aluminum or stainless steel. However, the present invention is not limited to this configuration as rigid wrist support 210 may be made of different materials in alternative embodiments, such as PVC, plastic, Teflon, thermoplastic or other materials.

Figure 3A:
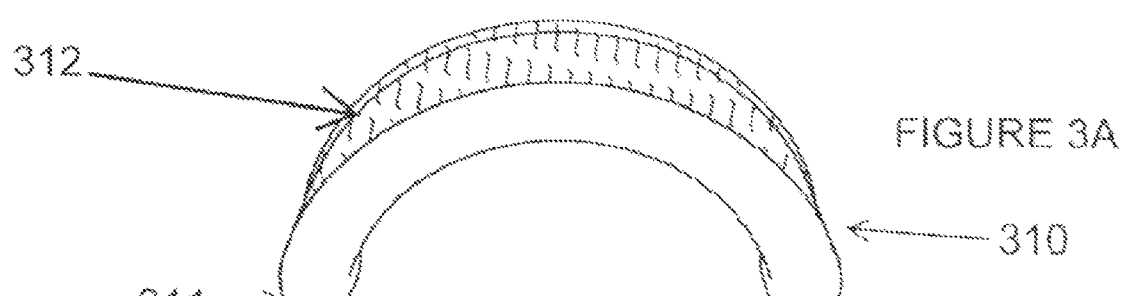
FIGS. 3A-3C illustrate a component of another alternative embodiment of present invention.
Figure 3B:
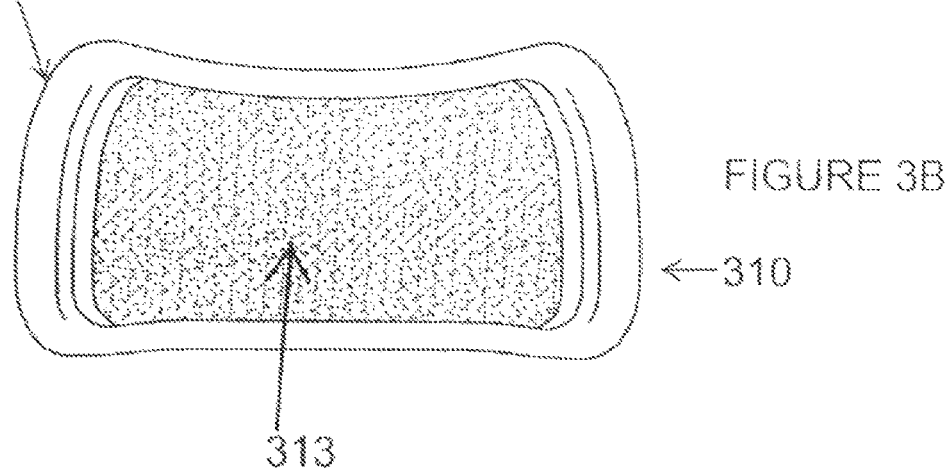
Figure 3C:
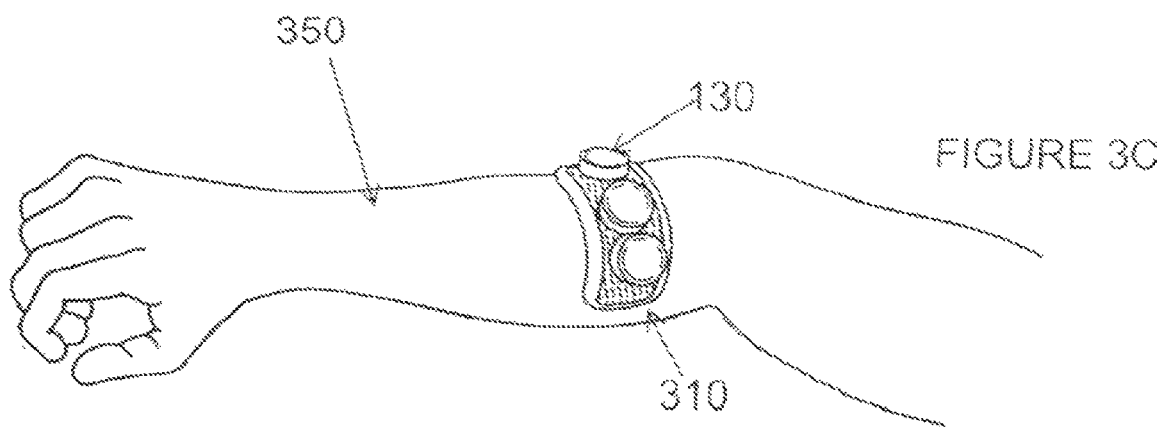

FIGS. 3A-3C illustrate forearm base member 310 of an alternative embodiment of anti-tremor orthotic system 100. In an alternative embodiment, forearm base member 310 may be utilized alone or in addition to the components illustrated in FIGS. 1A-1D. Forearm base member 310 is sized and configured to contour to the shape of a user's forearm 350 near the elbow as illustrated in FIG. 3C.

In one embodiment of the present invention, as illustrated in FIGS. 3A—3C, forearm base member 310 may also include a cushioning area 311 that surrounds the outer boundaries of forearm base member 310 to provide comfort to its user. Cushioning area 311 may be an area of forearm base member 310 that includes foam or some other soft material to provide a soft or cushioning feeling to a user for the purpose of providing comfort to a user. In one embodiment, cushioning area 311 may be configured with a thickness and height to provide space between base member 310 and a user's skin to allow for air flow between forearm base member 310 and user's skin to assist in reducing the amount of perspiration and to increase a user's comfort level.

As illustrated in FIG. 3A, forearm base member 310 is also configured with a landing area 312 located on the outer side of forearm base member 310. Landing area 312 provides an area for the placement of weighted members 130 as illustrated in FIG. 3C. In one embodiment of the present invention, forearm base member 310 is configured so that landing area 312 is covered with some type of fastening material that is attached to the back side of forearm base member 310 and is suitable for receiving and holding various types of weighted members 130 as illustrated in FIG. 3C.

FIG. 3B illustrates an underside view of forearm base member 310. The underside of forearm base member 310 includes an underside cushioning area 313. Underside cushioning area 313 is an area of forearm base member 310 that will likely come into contact with a user's forearm when in use. In one embodiment, cushioning area 313 is configured so that it includes foam or some other soft material to provide a soft or cushioning surface so that when forearm base member 310 is in use, a user will feel the softness of cushioning area 313. While foam may be used to provide comfort to a user at cushioning area 313, the present invention is not limited to foam, such as closed cell foam, as any number of soft materials may be used to provide cushioning, such as cotton, gel packs, felt, bubble materials, and the like.

FIG. 3C illustrates forearm base member 310 positioned on a user's forearm 350 with weighted members 130 connected to landing area 312 of forearm base member 310. Weighted members 130 may be of any number of different shapes and sizes. Forearm base member 310 with weighted members 130 illustrated in FIGS. 3A-3C of an alternative embodiment of anti-tremor orthotic system 100 assist in reducing a user's tremors of the palm involuntarily moving from a palm-up or supination to a palm-down or pronation position. Users experiencing tremors may suffer from excessive contraction of the supinator and pronator muscles that often cause the forearm to rotate back and forth with the palm of the user's hand moving from a palm-up to a palm-down position involuntarily. As illustrated in FIG. 3C, weighted members 130 and forearm base member 310 assist to reduce tremors and excessive involuntary muscle contraction of supinator and pronator muscles in addition to long flexor and extensor muscles.

In one embodiment, the present invention is configured so that the size and configuration of forearm base member 310 allows weighted members 130 of different sizes to be placed on landing area 312. Similar to the weighted members 130 illustrated in FIG. 1C, weighted members 130 in FIG. 3C may be cylindrical disks made of some type of non-toxic materials, such as aluminum or stainless steel, that are configured in 2 ounce increments, or any various incremental size, for ease of placement and removal. Similar to landing area 122 of base member 120 of FIG. 1A, landing area 312 may be configured with any number of different fastening materials to create a connection membrane for securing items such as weighted members 130 and allowing weighted members 130 to be easily moved, removed, replaced, or additional weighted members 130 added with little to no difficulty. In one embodiment of the present invention, landing area 312 may be configured with a fastening material such as hook and loop fasteners whereby one component of the hook and loop fasteners, such as the hooks, is attached to landing area 312 and the second component of the hook and loop fastener, such as the loops, is attached to weighted members 130 so that weighted members 130 may be securely connected to landing area 312 of forearm base member 310. In alternative embodiments, landing area 312 may be configured so that the surface of landing area 312 is magnetic and weighted members 130 are also magnetic so that weighted members 130 may be various size magnets or some type of magnetic material which would allow a user to easily remove and add additional weighted members 130 in a quick and easy manner to accommodate a user's needs to add or remove weight as needed.

In one embodiment, the present invention is configured so that weighted members 130 may be easily removed or moved to different locations on landing area 312 of forearm base member 310. In addition, weighted members 130 may be easily removed and replaced with different size weighted members 130 (heavier or lighter). Different size weighted members 130 may be used to replace or add to any existing weighted members 130 to assist with the effectiveness of reducing tremors.

Figure 4A:
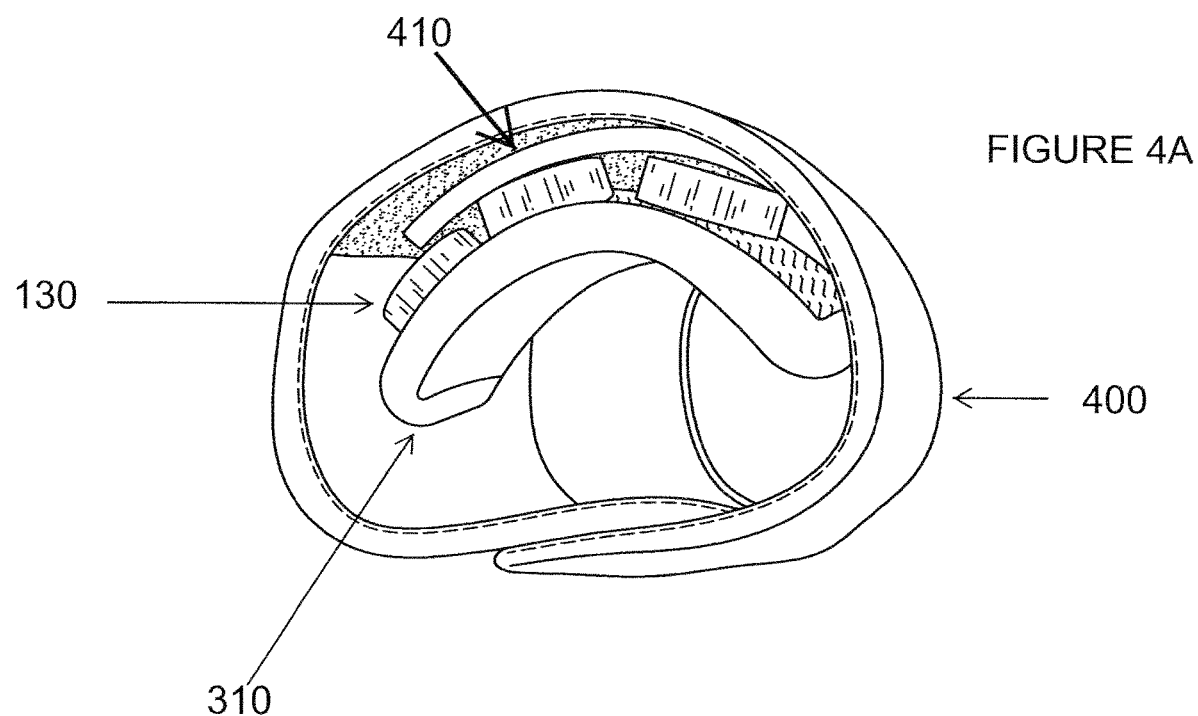
FIGS. 4A-4B is an illustration of an alternative embodiment of the present invention including the component illustrated in FIGS. 3A-3C.
Figure 4B:
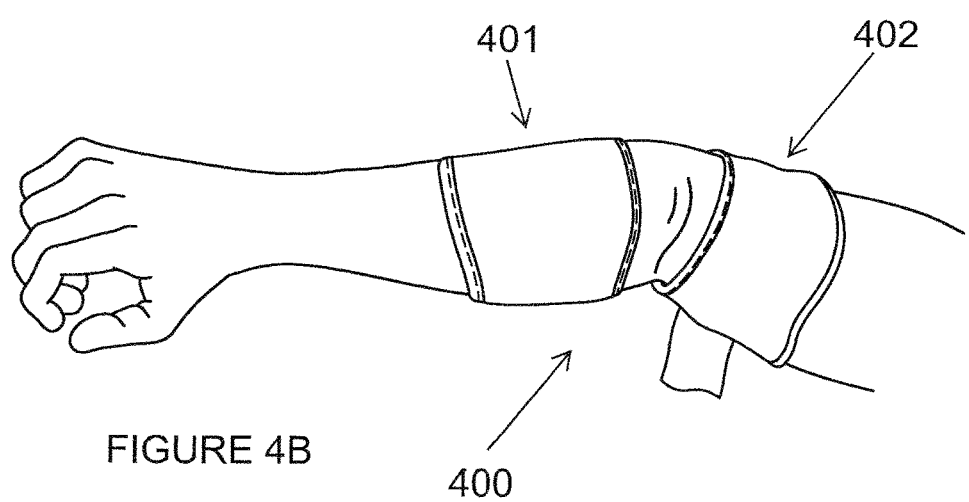

FIGS. 4A-4B illustrate compression cover 400 utilized in one embodiment of anti-tremor orthotic system 100. Compression cover 400 functions to cover forearm base member 310 and weighted members 130 attached to forearm base member 310. As illustrated in FIG. 4A, compression cover 400 may include an attachment area 410 for attaching forearm base member 310 to cover 400. In one embodiment, anti-tremor orthotic system 100 is configured so that attachment area 410 and weighted members 130 attach to one another with the use of hook and loop fasteners. In such an embodiment, one component of the hook and loop fasteners, such as the hooks, is attached to attachment area 410 and the second component of the hook and loop fastener, such as the loops, is attached to weighted members 130 so that weighted members 130 may be securely connected to attachment area 410 of compression cover 400. With this attachment, forearm base member 310, weighted members 130, and compression cover 400 are securely fastened to one another to increase the effectiveness of the present invention and to also allow a user to freely move his/her elbow and arm without having to worry about compression cover 400, forearm base member 310, or weighted members 130 moving and coming off or loose when in use. Such a secure connection of compression cover 400, forearm base member 310, and weighted members 130 to one-another and to a user's arm also allow for an unrestricted and free range of motion for the user. The use of compression cover 400 also provides users with the ability to adjust the location of forearm base member 310 and allows users to quickly and easily remove the components and wash/clean the various components.

In one embodiment, as illustrated in FIG. 4B, compression cover 400 is configured with a distal member 401 and a proximal member 402. Distal member 401 wraps around forearm base member 310 and assists in holding forearm base member 310 in the correct location on a user's forearm. Proximal member 402 wraps around a user's arm above or near the elbow crease and also assists in holding compression cover 400 in a fixed location on a user's arm. This configuration allows a user to have a full range of motion when moving an arm, such as bending and straightening an arm at the elbow, and functions to keep forearm base member 310 in its desired location so that a user will experience the benefit of reduced tremors and not be restricted from moving the arm while compression cover 400 is in use. In one embodiment, compression cover 400 is made of some type of nylon, neoprene, and/or spandex material so that compression cover 400 will provide some level of compression and fit snuggly over a user's forearm, but will not be overly tight or discomforting to a user. However, the present invention is not limited to this configuration as in other embodiments, compression cover 400 may be made of different types of materials, such as leather, rubber, or latex along with some additional components to assist in holding compression cover 400 securely over forearm base member 310 and weighted members 130.

Figure 5A:
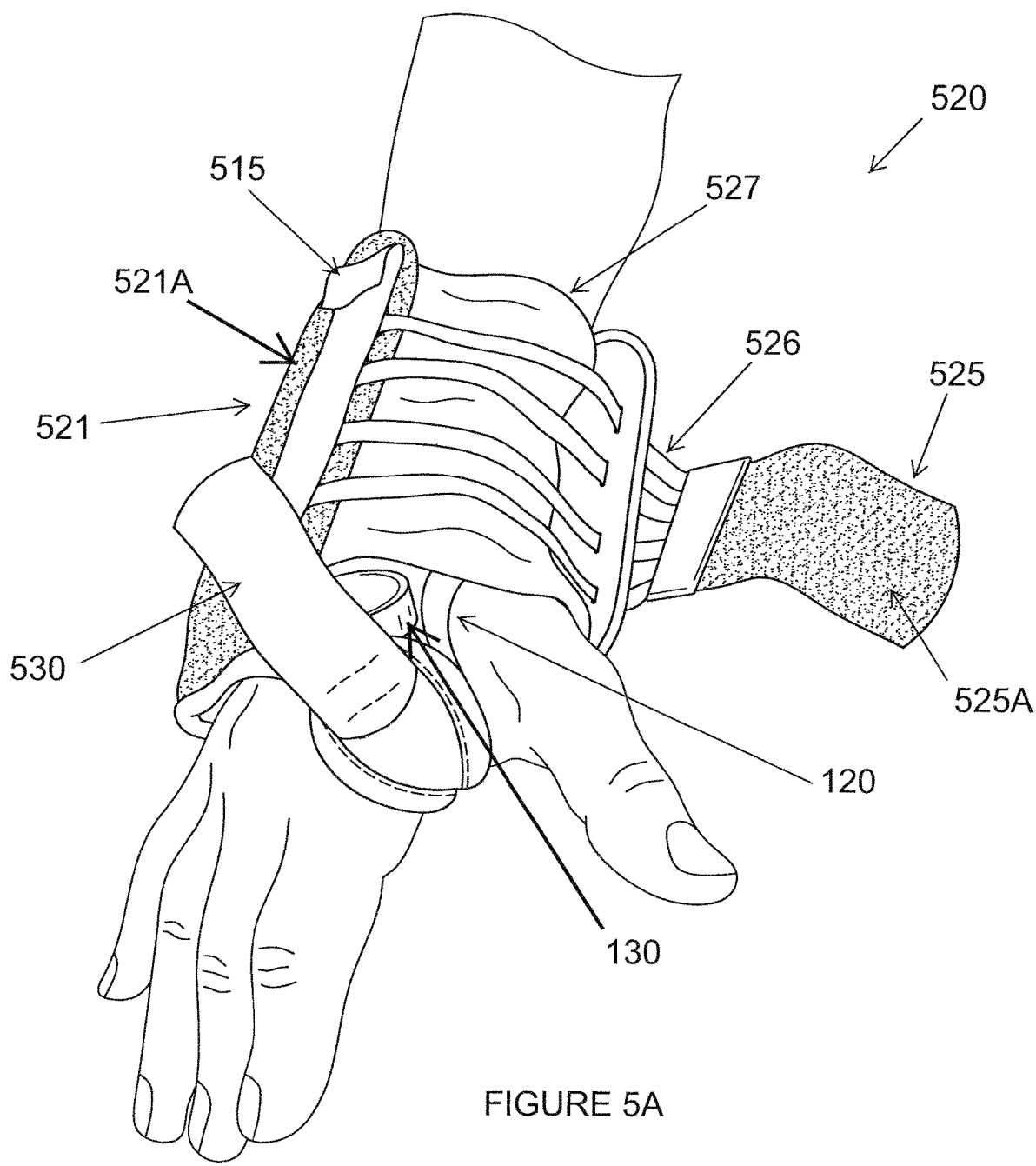
FIGS. 5A-5B illustrate another embodiment of the present invention.
Figure 5B:
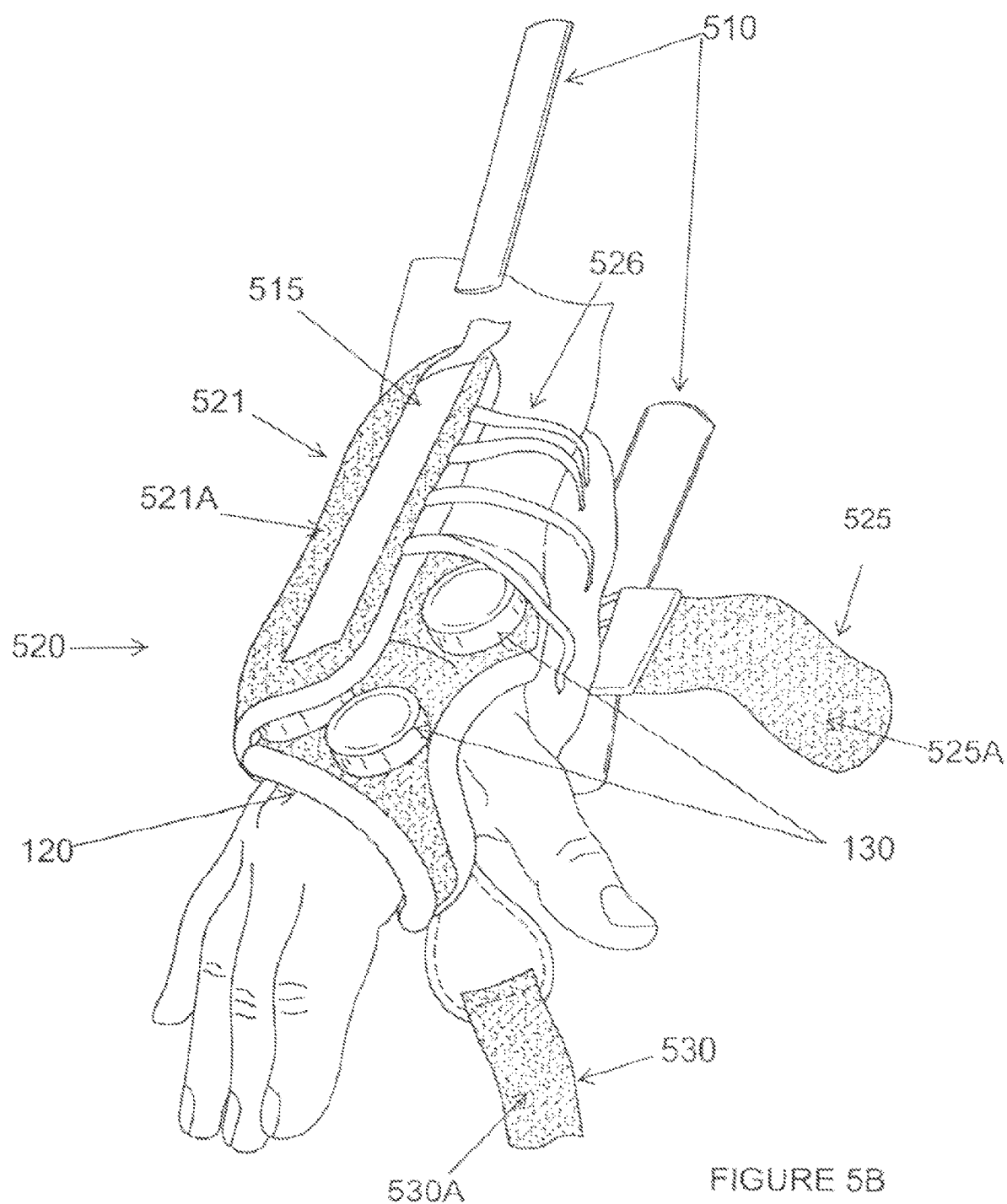

FIGS. 5A-5B illustrate another embodiment of the present invention. The embodiment illustrated in FIGS. 5A-5B includes a wrist support member 520. Wrist support member 520 may be made of any number of different materials, such as nylon, leather, spandex, neoprene, and the like. Wrist support member 520 assists in reducing tremors of various patients experiencing severe tremor disorders. Wrist support member 520 may be configured with laces 526, covering member 527, and straps 525 and 530. One of straps 525 and 530 may be located to extend over the web space or purlicue between the thumb and index finger as illustrated by strap 530. However, the present invention is not limited to this configuration. Laces 526 and straps 525 and 530 assist in securing wrist support member 520 to a user's hand/wrist area as illustrated in FIGS. 5A-5B. Covering member 527 acts to protect and cover a user's hand/wrist area to cover and protect a user's hand/wrist from laces 526 and to also cover and help secure any additional items that may be placed on a user's hand/wrist under wrist support member 520, such as base member 120 as illustrated in FIGS. 5A-5B. In alternative embodiments, the present invention may be configured without covering member 527. FIG. 5B is illustrated without covering member 527 to clearly illustrate the placement of base member 120 under wrist support member 520.

In one embodiment, wrist support member 520 is configured with an outer layer 521. Outer layer 521 may be configured with a fastening material such as hook and loop fasteners illustrated as 521A in FIGS. 5A-5B whereby one component of the hook and loop fasteners, such as the hooks, is attached to landing area 521 as illustrated by 521A in FIGS. 5A-5B and the second component of the hook and loop fastener, such as the loops, is attached to straps 525 and 530, as illustrated by 525A and 530A in FIGS. 5A-5B, so that straps 525 and 530 may be securely connected to outer layer 521 of wrist support member 520. The present invention is not limited to the use of hook and loop fasteners on wrist support member 520 as any number different securing mechanisms may be used to secure wrist support member 520 to a user's hand/wrist such as a zipper, buttons, and the like. When straps 525 and 530 are securely fastened to outer layer 521, laces 526 are pulled together to fasten and secure wrist support member 520 to a user's hand/wrist so that wrist support member 520 will be securely fastened to a user's wrist/hand when in use. When straps 525 and 530 are securely fastened to outer layer 521 and laces 526 are pulled together, covering member 527 provides a protective covering to a user's hand/wrist so that laces 526 will not be directly touching or rubbing up against a user's skin.

In one embodiment, wrist support member also includes removable support members 510 and pocket members 515 as illustrated in FIGS. 5A-5B. Support members 510 are preferably rigid volar and/or dorsal support members that will slide into and/or be located within pocket members 515. Pocket members 515 may be attached to outer layer 521 of wrist support member 520. In an alternative embodiment, one pocket member 515 may be attached to outer layer 521 and another pocket member may be attached to covering member 527. In one embodiment, support members 510 will cross a user's wrist joint to reduce a user's tremors. In one embodiment, support members 510 maybe made of some type of metal, such as aluminum or stainless steel. However, the present invention is not limited to this configuration as support members 510 may be made of different materials in alternative embodiments, such as PVC, plastic, Teflon, thermoplastic or other materials.

In one embodiment, wrist support member 520 is slid over a user's hand/wrist and over base member 120 with weighted members 130 as illustrated in FIGS. 5A and 5B. Thus, base member 120 with weighted members 130 would be positioned over a user's hand and then wrist support member 520 would be positioned over base member 120. Wrist support member 520 with the dual rigid and removable support members 510 in conjunction with base support member 120 and weighted members 130 act to immobilize and support a user's wrist and thereby reduce tremors by producing a counterforce and sensory inhibition and creating a fulcrum and an inhibition of the superficial extensor tendons on the back of the user's hand to reduce a user's tremors. In addition, wrist support member 520 and base member 120 act together to stabilize a user's wrist and prevent wrist flexion, extension, radial deviation, and ulnar deviation while still allowing a user to have the benefits of full grasp with prehension unrestricted. While FIGS. 5A-5B illustrate wrist support member 520 positioned over base member 120 and weighted members 130, the present invention is not limited to such a configuration as wrist support member 520 and base member 120 may be configured as one component that slides over a user's hand/wrist to assist in reducing tremors.

Figure 6:
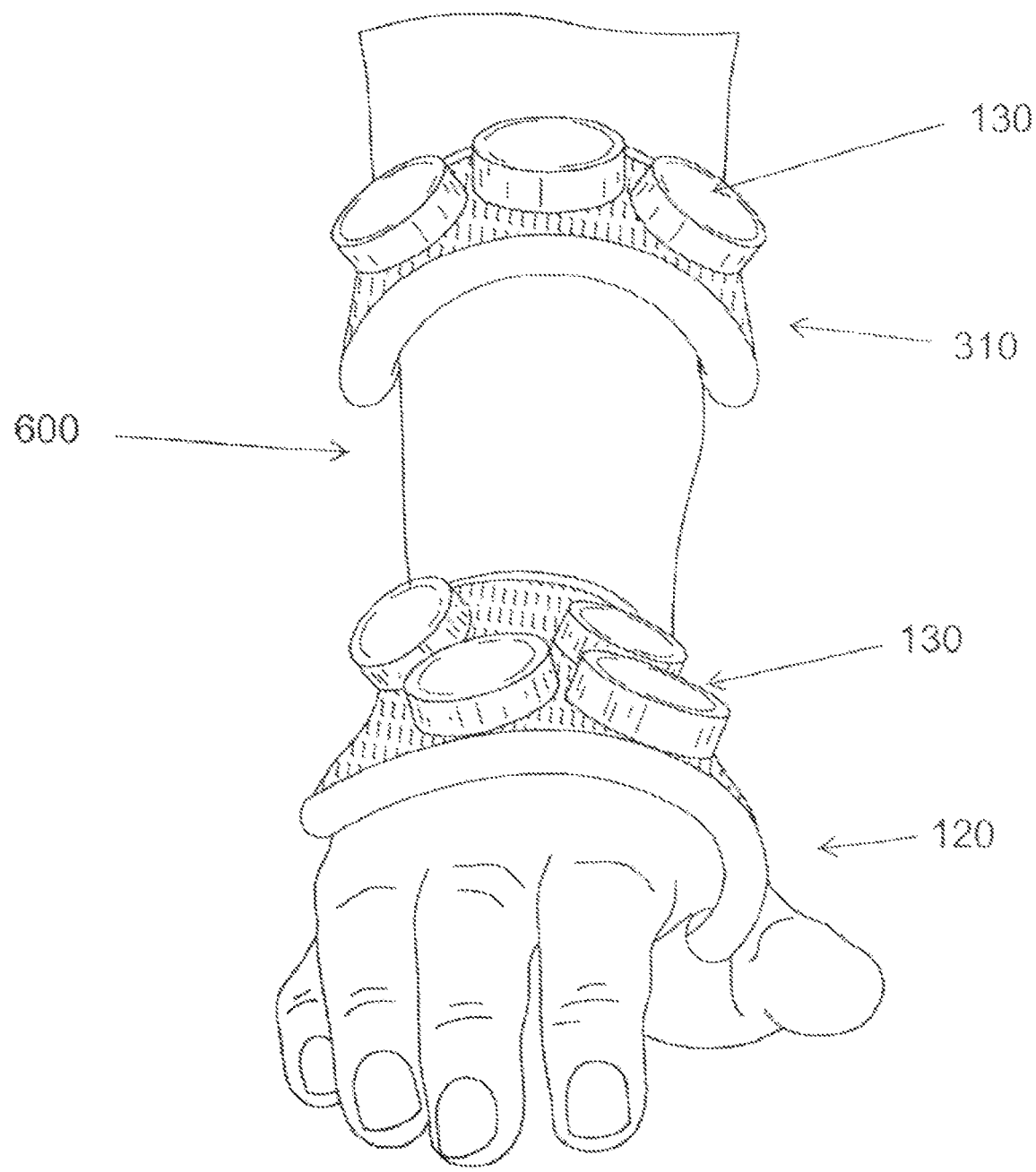
FIG. 6 is an illustration of another embodiment of the present invention.
Figure 7:
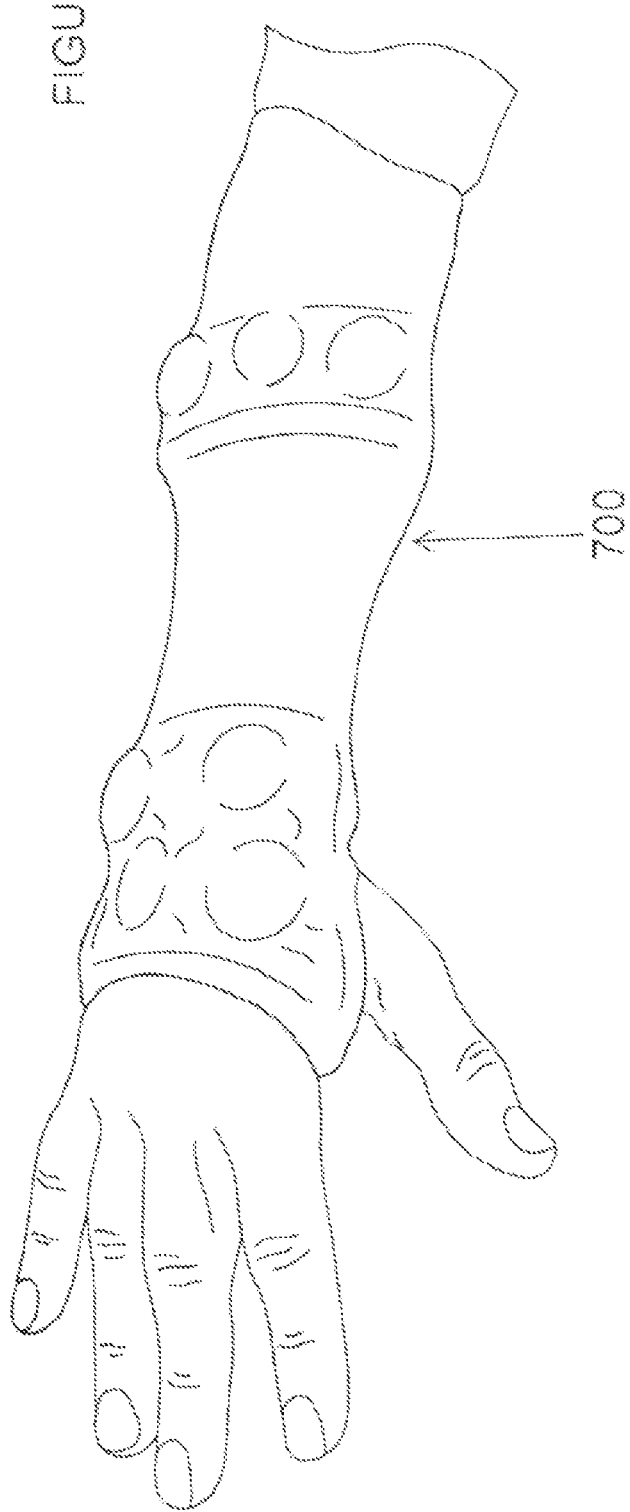
FIG. 7 is another illustration of the embodiment illustrated in FIG. 6.

FIG. 6 illustrates portions of an embodiment of anti-tremor orthotic system 100 whereby both base member 120 to be located on the hand of a user and forearm base member 310 to be located on the forearm of a user's hand and arm 600 of FIG. 6 are utilized to reduce tremors. In such an embodiment, forearm base member 310 with weighted members 130 will be placed upon a user's forearm while base member 120 with weighted members 130 will be placed upon the hand area of a user as illustrated in FIG. 6. FIG. 7 illustrates an embodiment of the present invention illustrated in FIG. 6 fitted on a user with long compression cover 700. In such an embodiment, anti-tremor orthotic system 100 includes base member 120 with weighted members 130 fitted on a user's hand and forearm base member 310 with weighted members 130 fitted on a user's forearm. In such an embodiment, long compression cover 700 is used to hold both base member 120 and forearm base member 310 in position without the need for compression cover 400 or cover member 110. In such an embodiment, long compression cover 700 may be used instead of compression cover 400 and cover member 110.

In an embodiment of the present invention comprising both the hand and arm components illustrated in FIGS. 6 and 7, the components of anti-tremor orthotic system 100 illustrated in FIGS. 1 and 1A-1D and FIGS. 4A-4B operate to reduce flexion/extension tremors in a user's hand while at the same time reducing excessive muscle contraction of the supinator and pronator muscles thereby reducing tremors of the forearm rotating back and forth from a palm up/palm down position. In such an embodiment, the combination and arrangement of these various components of anti-tremor orthotic system 100 (weighted members 130, base member 120, and cover member 110, base member 310, compression cover 400 and/or long compression cover 700) work together to produce a sensory inhibition and create a fulcrum and an inhibition of the superficial extensor and abductor tendons on the user's hand dorsally to reduce tremors in a user's hand and also work together to produce a sensory inhibition and create a fulcrum in the supinator and pronator muscles to reduce tremors of a user's forearm rotating back and forth from a palm up/palm down position.

Long compression cover 700 is configured to keep base member 120 and forearm base member 310 and weighted members 130 in the desired locations so that a user will experience the benefit of reduced tremors and compression cover 700 will not affect a user's range of motion of the hand and arm while long compression cover 700 is in use. In one embodiment, long compression cover 700 may be made of some type of nylon, neoprene, and/or spandex material so that long compression cover 700 will provide some level of compression and fit snuggly over a user's hand and forearm, but will not be overly tight or discomforting to a user. However, the present invention is not limited to this configuration as in other embodiments, long compression cover 700 may be made of different types of materials.

While long compression cover 700 of FIG. 7 is illustrated as one continuous member that slides over a user's hand and onto the arm, the present invention is not limited to this configuration. In alternative embodiments, long compression cover 700 may be configured with a zipper or other similar mechanism to allow users to use long compression cover 700 and properly use long compression cover 700 without having to stretch it over the hands, wrist and arm. Rather, a user could unzip the zipper and position long compression cover 700 in the proper position and then zip up the zipper so that long compression cover 700 can apply the needed compression of tightness to hold base member 120 and forearm base member 310 and weighted members 130 in the proper location. In one embodiment, compression cover 700 may also include straps that may be located at the wrist and forearm areas to assist in properly holding compression cover 700 in the desired location. In another embodiment, compression cover may also include internal pockets to house base member 120 and forearm base member 310 to assist in holding these components in the desired location along a user's hand and forearm. Long compression cover 700 may also be configured with various elastic members with buttons located at the most proximal aspect of long compression cover 700 to ensure proper fit around a user's upper arm and to assist in preventing long compression cover 700 from sliding down a user's arm when in use. The configurations discussed herein are merely a few examples and not limitations of the present invention as long compression cover 700 may be configured with any number of different connection means and/or fastening mechanisms to assist in holding long compression cover 700 in place on a user's arm when in use.

Figure 8:
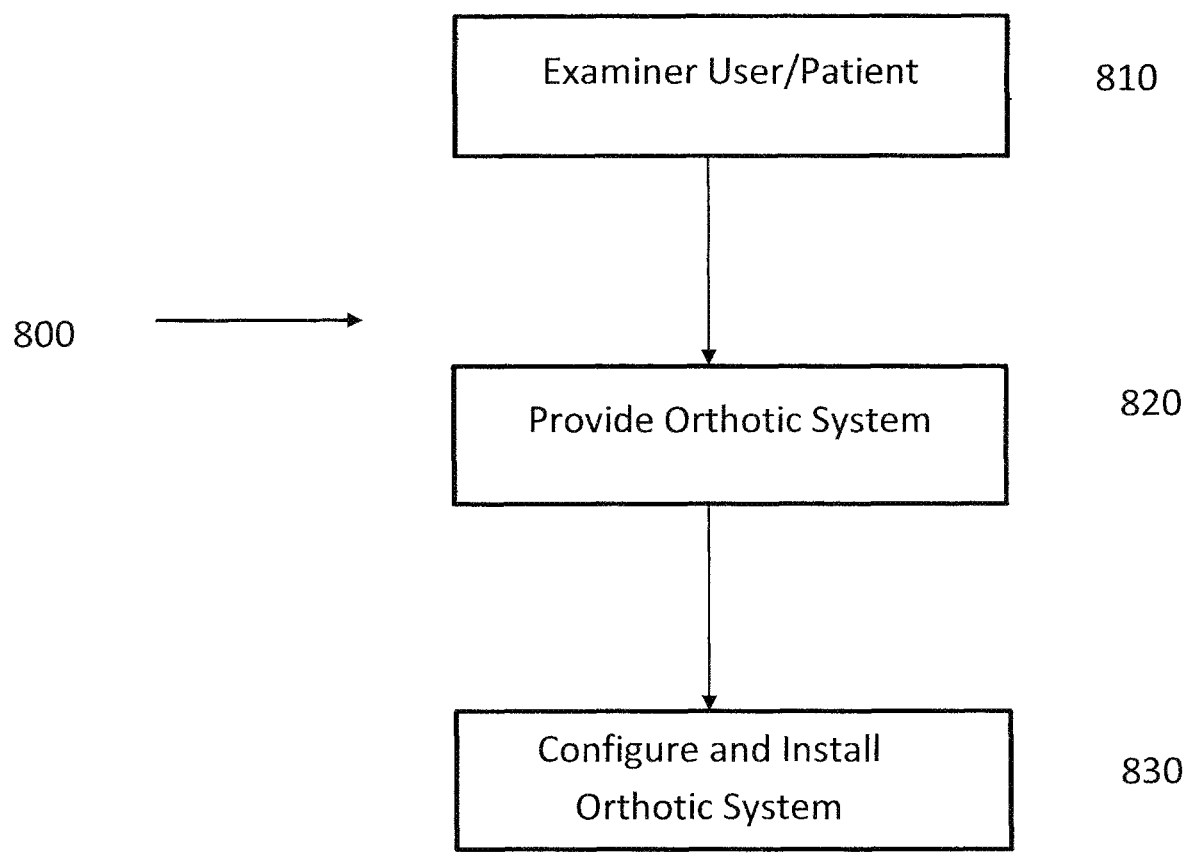
FIG. 8 illustrates a flowchart representing one method for reducing tremors according to one embodiment of the present invention.

FIG. 8 illustrates a flowchart representing one method for reducing tremors according to one embodiment of the present invention. Flow 800 represents a method for reducing tremors. In block 810 a user/patient is examined for tremors. The examination will include an examination of the user/patient by a trained professional whereby the examiner will analyze a user with tremors and look for the presence of various tremors such as flexion/extension and/or rotational tremor patterns that dominate causing the user to have difficulty performing functional tasks. The examiner may also perform a screening of the user/patient for possible adverse reactions/contraindications, including but not limited to: severe arthritis unmanaged, acute fracture, acute shoulder/arm/hand injury, unmanaged pain in upper extremity, and/or allergies. After examination, flow 800 proceeds to block 820 where anti-tremor orthotic system 100 is provided.

In block 820, an anti-tremor orthotic system 100, as discussed herein is provided. Part of providing anti-tremor orthotic system 100 will include the manufacture of base member 120 and forearm base member 310, if needed by a user, so that the components will properly fit a user. Base member 120 and/or forearm base member 310 may be manufactured by a custom process for a user or through a pre-fabricated process. In one method of the present invention, part of providing the anti-tremor orthotic system 100 will include taking various measurements from a user. For example, in one method of manufacture, a user's hand is traced marking all phalange joint lines, wrist crease, base of thumb, and ulnar styloid process. Then a user's hand pattern is traced onto a suitable material for the orthotic, such as a thermoplastic material, which material is then cut, heated, and molded over the back of user's hand respecting all bony prominences and either clearing or crossing joint lines depending on the type of tremor present and severity of the user's tremor. In one embodiment, the method may also include the creation of forearm base member 310 when a rotational tremor is present. In such an embodiment, a material, such as thermoplastic, is heated and molded distal to user's elbow crease covering approximately half of user's forearm circumference and at a width suitable for the user, such as a width of approximately 2-3 inches. The material is then configured so that any flares are rounded to avoid any pressure or discomfort for the user. After anti-tremor orthotic system 100 is provided, flow 800 proceeds to block 830, where anti-tremor orthotic system 100 is configured for a user.

After base member 120 is properly manufactured and configured to properly fit a user, flow 800 proceeds to block 830 where anti-tremor orthotic system 100 is properly configured and installed for and on a user. In properly configuring and installing anti-tremor orthotic system 100, base member 120 is properly configured and positioned upon a user so that it properly fits a user and weighted members 130 are selected and properly positioned upon base member 120, and cover member 110 is properly positioned over base member 120 to secure base member 120 to a user. In an embodiment of anti-tremor orthotic system 100 that will include forearm base member 310, forearm base member 310 is properly configured and positioned upon a user so that it properly fits a user and weighted members 130 are selected and properly positioned upon forearm base member 310 and compression cover 400 may be properly positioned over forearm base member 310. In an alternative method whereby both base member 120 and forearm base member 310 are utilized, configured, and installed on a user, then cover member 700 may be provided and properly positioned over base member 120 and forearm base member 310 to secure base member 120 and forearm base member 310 to the user. In such a method, cover member 110 and compression cover 400 will likely not be used.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for reducing tremors consisting of:
   examining a patient for tremors;
   providing a system for reducing tremors comprising:
      a rigid base member configured to fit over a portion of the back side of a patient's hand said rigid base member comprising:
         outer edges;
         an outer side with a landing area;
         an underside;
         an expansion member wherein said expansion member is sized to fit between a patient's thumb and index finger into the web space or purlicue between the thumb and index finger of a patient; and
         a flared out area wherein said flared out area projects posteriorly to account for the ulnar styloid bone of a patient to reduce rubbing of said base member against said ulnar styloid bone;
      at least one weighted member wherein said at least one weighted member is positioned directly on said landing area of said outer side of said rigid base member;
      a fastening mechanism wherein said fastening mechanism operates to
   attach said at least one weighted member directly to said landing area of said outer side of said rigid base member; and
      a covering member wherein said covering member covers said rigid base member and said at least one weighted member and acts to secure said rigid base member to said patient's hand;
   configuring said system for reducing tremors; and installing said system for reducing tremors on said patient.

2. The method of claim 1 wherein said covering member is comprised of one or more of:
neoprene;
spandex;
cotton;
nylon; or
leather.

\* \* \* \* \*